United States Patent [19]

Brezette

[11] 3,978,983

[45] Sept. 7, 1976

[54] CATHETERIZATION TRAY WITH LUBRICATION CHANNEL

[75] Inventor: Michael Warren Brezette, Roselle, Ill.

[73] Assignee: Abbott Laboratories, North Chicago, Ill.

[22] Filed: Nov. 4, 1974

[21] Appl. No.: 520,594

[52] U.S. Cl. .............................. 206/364; 128/348; 128/349 R; 206/210
[51] Int. Cl.² ................. B65D 85/08; A61M 25/00
[58] Field of Search ...................... 128/348–351; 206/210, 364

[56] References Cited
UNITED STATES PATENTS 2,346,636  4/1944  Porter ........................... 206/210 X
2,625,264  1/1953  Edwards ........................... 206/364
3,166,189  1/1965  Disston ............................ 206/364
3,329,261  7/1967  Serany et al. .................. 206/364 X
3,345,988  10/1967  Vitetto ........................... 128/349 R Primary Examiner—Lawrence W. Trapp
Attorney, Agent, or Firm—Aaron L. Hardt; Robert L. Niblack

[57] ABSTRACT

A urethral catheterization tray having at least one compartment for receiving a catheter and/or other implements useful in a catheterization procedure. The tray includes a lubrication channel recessed from its upper surface and adapted for lubricating that portion of the catheter to be inserted into a patient.

6 Claims, 6 Drawing Figures

CATHETERIZATION TRAY WITH LUBRICATION CHANNEL

BACKGROUND OF THE INVENTION

The present invention relates to the field of surgical trays, and more particularly, to surgical trays for use in urethral catheterization.

In surgical procedures which utilize urinary catheters, it is often necessary or desirable to lubricate the catheter before it is inserted into the patient. This lubrication of the catheter is desired for ease of insertion and care must be taken to lubricate the catheter in a sterile manner. Because the accurate positioning of a catheter with respect to the urethra requires the labia to be held apart or the penis to be manipulated, to avoid the necessity of having an assistant, the most efficacious sterile catheterization practice requires that the catheter must be lubricated and inserted with one hand.

Accordingly, there have been several previous attempts to provide catheters that are lubricated when removed from their packages for insertion into a patient. Attempts to lubricate the catheter at the time it is packaged have failed because the continuous contact of the lubricant with the catheter has a detrimental effect on the catheter while it is in storage. U.S. Pat. Nos. 3,345,988 to Vitello; 3,648,704 to Jackson; and 3,683,928 to Kuntz, each disclose a package providing means for lubricating a catheter as it is removed therefrom. Additionally, U.S. Pat. No. 3,726,281 to Norton, et al. discloses a self-lubricating catheter having means for lubricating itself as it is inserted into the patient.

A major disadvantage of the devices disclosed in the aforementioned patents is that most urethral catheters are presently packaged in their own sterile wrapper and a packet of lubricating jelly is included in the kit or tray containing that catheter. Accordingly, to employ the inventions of the aforementioned patents, it would be necessary for the present mode of supplying catheters and lubricating jelly to be abandoned and new equipment designed, purchased and employed. Therefore, it is more economical and preferable to maintain the present packages and methods.

Most of the present urethral catheterization trays or kits provide, inter alia, a sterile catheter, a packet of sterile lubricating jelly, and a sterile towel. The lubricating jelly is squeezed onto the towel and the catheter is then pushed through the jelly to lubricate it prior to insertion into the patient. When jelly is squeezed onto the towel, it is both absorbed by the towel and readily spread about the towel by the catheter as it is pushed through the jelly, thereby causing much of the jelly to be wasted.

Accordingly, a need still remains for a simple, efficient and effective means of lubricating a urethral catheter with one hand in a manner capable of facilitating sterile catheter insertion.

SUMMARY OF THE INVENTION

The primary object of the present invention, therefore, is to provide a means for lubrication of a urethral catheter that can be performed solely with one hand, while supplying the catheter and lubricating jelly in the package in which they are most commonly supplied at present. In accordance with this and other objects, there is provided by the present invention a tray useful for catheterization of a urethra and having an upper surface with at least one compartment recessed therefrom for receiving a catheter and/or other implements necessary to the catheterization. The tray has a lubrication channel recessed from its upper surface and adapted for lubricating that portion of the catheter which is to be inserted into the patient's urethra. Preferably, the width and depth of the lubrication channel are substantially equal to the diameter of the catheter. Further, the lower surface of the lubrication channel is preferably arcuate at one end to prevent the lubricant from being pushed out of the channel while the catheter is pushed therethrough.

BRIEF DESCRIPTION OF THE DRAWINGS

Other objects and more attendant advantages will become obvious to those skilled in the art by reading the following detailed description in connection with the accompanying drawing wherein like reference characters designate like or corresponding parts throughout the several figures thereof and wherein.

DESCRIPTION OF THE PREFERRED EMBODIMENT

Figure 1:
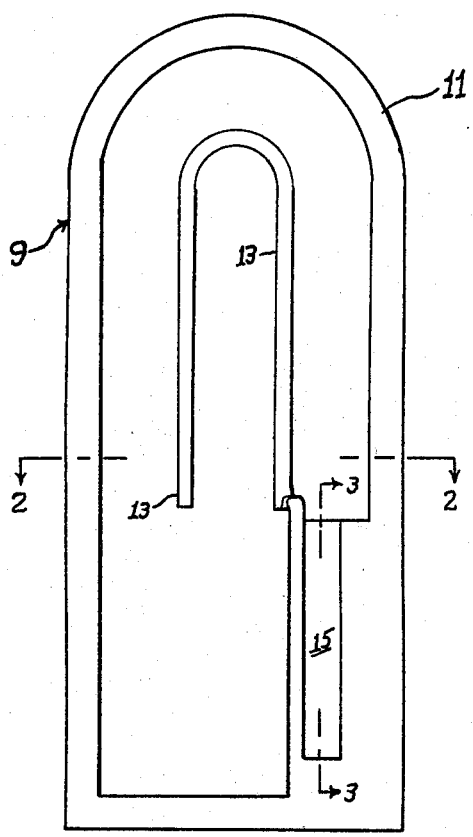
FIG. 1 is a top view of a tray including the lubrication channel of the present invention.
Figure 2:
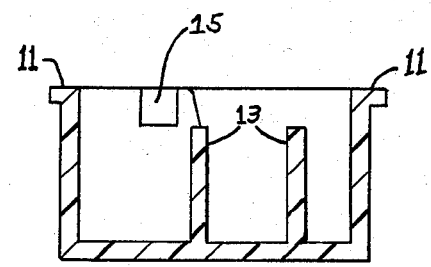
FIG. 2 is a cross-sectional view of the tray shown in FIG. 1 taken along the line 2—2 and showing the shape of the lubrication channel thereof.

Referring now to the drawing, there is generally shown in FIG. 1, a tray 9 useful for catheterization of a urethra and having an upper surface 11. Tray 9 can be made of any suitable material and most probably will be made of a plastic or a rigid foam. Recessed from upper surface 11 is a compartment which is further compartmentalized by a divider 13 to form a plurality of compartments for receiving a urethral catheter and/or other implements necessary to the catheterization. A lubrication channel 15 is recessed from upper surface 11 and adapted for holding a lubricant to be applied to the catheter. To obviate unnecessary spreading of the lubricant and possible bridging of the catheter over the channel because of the catheter's inherent rigidity, the width and depth of lubrication channel 15 are, preferably, substantially equal to the diameter of the catheter to be inserted. Thus, because most urethral catheters are calibrated on a French scale which is approximately 0.33 mm. per unit and because the largest urethral catheters commonly used are 30 French, channel 15 preferably is less than 12 mm.

Figure 3:
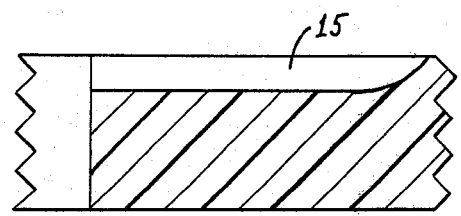
FIG. 3 is a cross-sectional view of the tray shown in FIG. 1 taken along the line 3—3 and showing the arcuate shape at one end thereof of the lower surface of the lubrication channel thereof.
Figure 4:
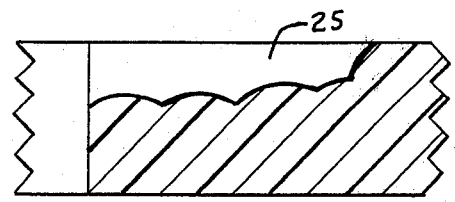
FIG. 4 is a cross-sectional view, similar to that of FIG. 3, showing the lower surface of another embodiment of the present invention.
Figure 5:
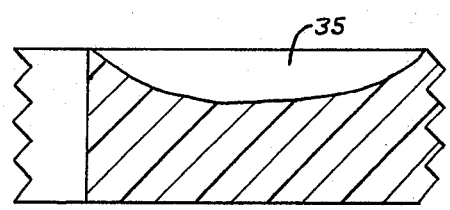
FIG. 5 is a cross-sectional view, similar to that of FIG. 3, showing the shape of the lower surface of still another embodiment of the present invention.

Lubrication channel 15 can be any length suitable for pushing or swirling the catheter through a lubricant that has been placed therein. Generally, such catheters are about 12 inches in length and lubrication channel 15 will not need to be more than 3 or 4 inches long. Advantageously, as shown in FIG. 3, lubrication channel 15 can be made in a manner such that its lower surface is arcuate at one end to prevent the lubricant from being pushed therefrom while the catheter is passed through the lubricant. Likewise, the lubrication channel 25 shown in FIG. 4 provides a lower surface of varying depth along its length and lubrication channel 35 shown in FIG. 5 provides a continuous arcuate lower surface along its entire length.

Figure 6:
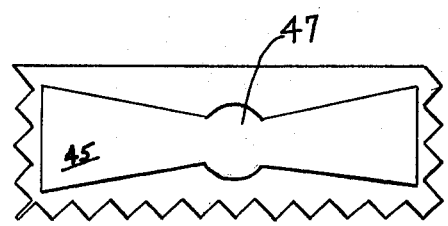
FIG. 6 is a partial top view of a tray showing the shape of still another embodiment of the lubrication channel of the present invention.

As shown in FIG. 6, a lubrication channel 45 having a width varying along its length can be made if so desired. Also, lubrication channel 45 can be provided with a cup-like area 47 to further facilitate the retention of a lubricant therein. Further, if desired, the width of the lubrication channel can be greater at its top than at its lower surface.

In practice, where a packet of lubricating jelly has been provided, it is opened and squeezed into lubrication channel 15. The catheter to be inserted into a urethra is then pushed or swirled through the lubricating jelly until the portion of the catheter to be inserted has been adequately lubricated. Because lubrication channel 15 confines the lubricant and is relatively impermeable to the lubricant, the channel provides better utilization of a given volume of lubricant when compared to the utilization provided by the prior art towel. Further, the tray need not be held in one hand while the catheter is being swirled through the channel 15.

While the present invention is most advantageous in that it can be used with presently known catheter and lubricant packages, if desired, lubrication channel 15 can also have a sterile lubricant packaged therein.

Having now described the invention in specific detail and exemplified the manner in which it may be carried into practice, it will be readily apparent to those skilled in the art, that innumerable variations, applications, modifications and extensions of the basic principles involved, may be made without departing from its sphere or scope.

That which is claimed is:

1. In a tray useful for catheterization of a urethra by a urethral catheter, said tray having an upper surface with at least one compartment recessed therefrom for receiving said catheter or other implements necessary to said catheterization; the improvement which comprises:

a lubrication channel for holding a lubricant while it is applied to said catheter, said channel recessed from said upper surface of said tray and closed at least at one end thereof, the length of said channel being substantially less than the length of said catheter and the lower surface of said channel arcuately rising to said upper surface at said closed end of said channel.

2. The tray defined in claim 1, wherein the width and depth of said channel are substantially equal to the diameter of said catheter.

3. The tray defined in claim 2, wherein said depth is less than 12 millimeters.

4. The tray defined in claim 1, wherein said lower surface is arcuate along its entire length.

5. The tray defined in claim 1, wherein the width of said lubrication channel is greater at the top than at the bottom thereof.

6. The tray defined in claim 1, wherein the width of said lubrication channel varies along its length.

* * * * *